United States Patent [19]

Kalb

[11] Patent Number: 5,743,893
[45] Date of Patent: Apr. 28, 1998

[54] DEVICE FOR COLLECTION OF VAGINAL DISCHARGE

[76] Inventor: Irvin M. Kalb, 113 Seagull La., Sarasota, Fla. 34236

[21] Appl. No.: 708,000

[22] Filed: Oct. 2, 1996

[51] Int. Cl.⁶ ............................................. A61M 1/00
[52] U.S. Cl. ........................... 604/317; 604/327; 604/330
[58] Field of Search ............................. 604/11, 358, 330, 604/331, 328, 329, 317, 319, 327

[56] References Cited

U.S. PATENT DOCUMENTS

| | | | |
|---|---|---|---|
| 3,128,767 | 4/1964 | Nolan | 604/330 |
| 3,216,422 | 11/1965 | Steiger et al. | 604/330 |
| 3,983,874 | 10/1976 | Davis et al. | 604/330 |
| 4,018,225 | 4/1977 | Elmi | 604/330 |
| 4,818,600 | 4/1989 | Braun et al. | 604/330 |
| 4,955,875 | 9/1990 | Knowles | 604/331 |
| 5,073,365 | 12/1991 | Katz et al. | 424/489 |
| 5,231,992 | 8/1993 | Leon | 604/330 |
| 5,295,984 | 3/1994 | Contente et al. | 604/317 |

*Primary Examiner*—John G. Weiss
*Assistant Examiner*—Ki Yong O
*Attorney, Agent, or Firm*—Bartony Hare & Edson

[57] ABSTRACT

The present invention provides a intravaginal collection device for the collection of vaginal discharge. The present collection device comprises a first layer that allows the passage of fluid therethrough but substantially prevents the passage of tissue and blood cells therethrough. The perimeter of the first layer is attached to a resilient rim. The rim is sufficiently resilient to provide an outward resilient force suitable to maintain the device in position within a user's vaginal canal during use. The device also comprises a second layer attached at its perimeter to the resilient rim. The second layer is suitable to substantially prevent the passage of fluid therethrough. The device further comprises a fluid retention layer positioned between the first layer and the second layer. The fluid retention layer is suitable for retaining fluid passed through the first layer. Tissue and blood cells are collected at the first layer of the present device, while vaginally discharged fluids are retained by the intermediate fluid retention layer. Vaginally discharged tissue and blood cells collected by the present device can be easily transported to health care professionals for pathological study.

8 Claims, 2 Drawing Sheets

DEVICE FOR COLLECTION OF VAGINAL DISCHARGE

FIELD OF THE INVENTION

The present invention relates to a feminine hygiene device, and, particularly, to a intravaginal device for the collection of vaginal discharge.

BACKGROUND OF THE INVENTION

For many years, sanitary napkins and tampons were the only types of commercially available menstrual collection products. Sanitary napkins, however, present a number of disadvantages including discomfort to the user, odor, leakage and disposal problems. The use of sanitary napkins can also result in problems with contamination and infection. Likewise, tampons also present numerous disadvantages. For example, tampons may not prevent leakage, may irritate the vagina, and may lead to serious infections.

Numerous attempts at designing internal vaginal discharge collection devices have failed as a result of poor performance, risk of infection and/or difficulty of use. A recent design purportedly reducing such problems is disclosed in U.S. Pat. No. 5,295,984 (Contente et al.). The device of Contente et al. comprises an elastomeric rim and a flexible film (for example, latex) reservoir. An absorbent pad of cotton fiber or other absorbent material may be placed within the collection space defined by the rim and reservoir. The absorbent pad may be impregnated with a drug to be delivered into the vagina. Still a number of problems, including lack of capacity, poor performance and difficulty of use, persist with current discharge collection devices.

It is thus very desirable to develop improved vaginal discharge collection devices that minimize or substantially eliminate such problems.

SUMMARY OF THE INVENTION

Generally, the present invention provides a collection device comprising a first layer adapted to allow the passage of fluid therethrough while substantially preventing the passage of tissue and blood cells therethrough. The perimeter of the first layer is attached to a resilient rim. The rim is sufficiently resilient to provide an outward resilient force suitable to maintain the device in position within a user's vaginal canal during use. The device also comprises a second layer attached at its perimeter to the resilient rim. The second layer is adapted to substantially prevent the passage of fluid therethrough. The device further comprises a fluid retention layer positioned between the first layer and the second layer. The fluid retention layer is suitable for retaining fluid passed through the first layer.

DETAILED DESCRIPTION OF THE INVENTION

Figure 1:
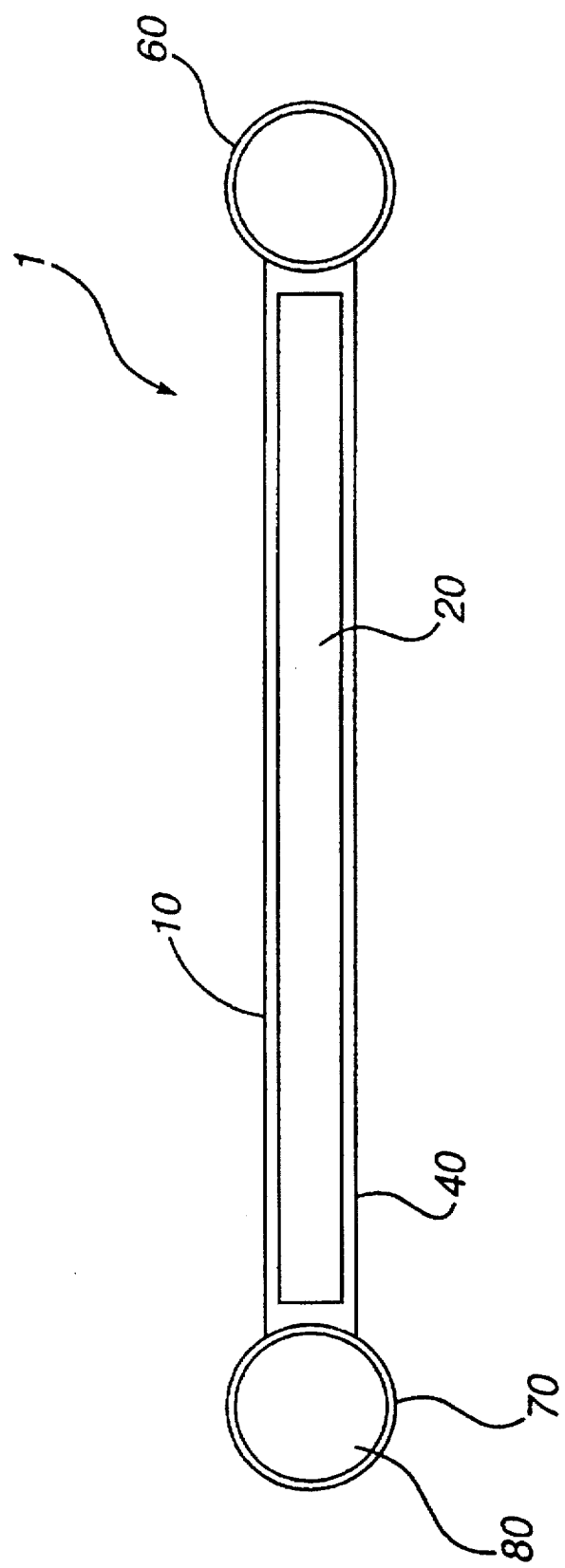
FIG. 1 illustrates a flat, side cross-sectional view of an embodiment of the present invention.
Figure 2:
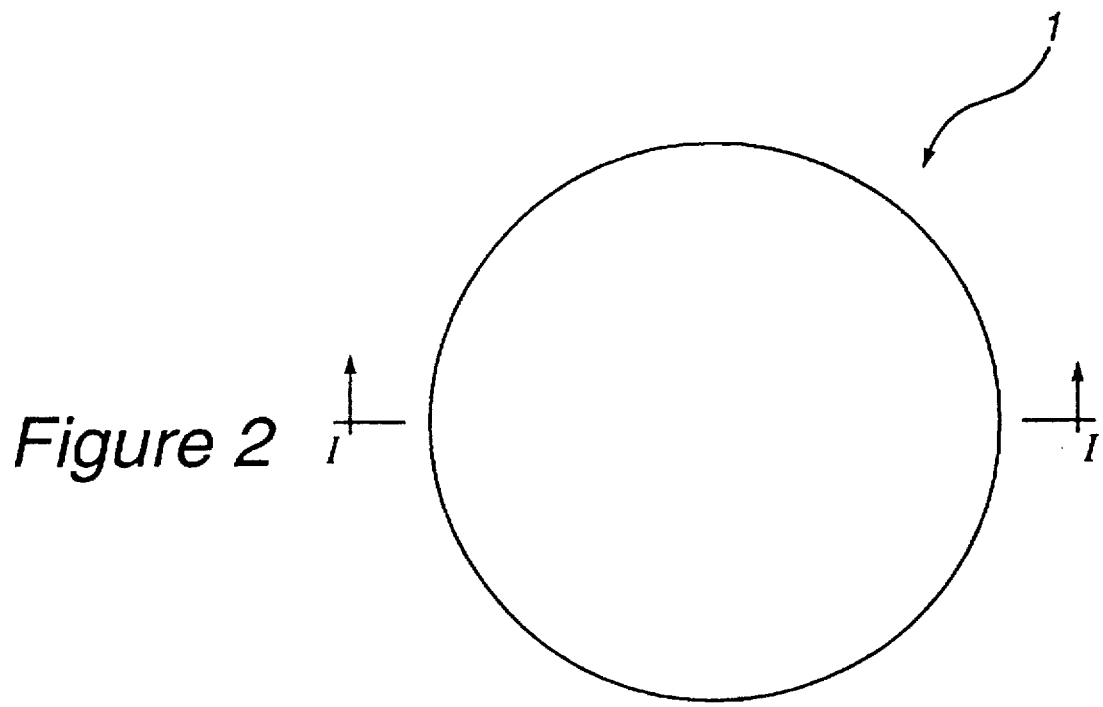
FIG. 2 illustrates a plan view of the embodiment of FIG. 1.
Figure 3:
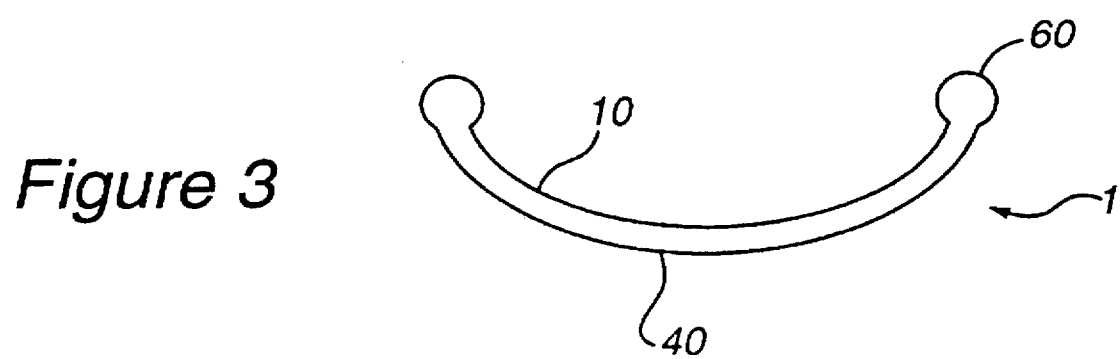
FIG. 3 illustrates a side view of the embodiment of FIG. 1 as inserted into the vagina.

As illustrated in FIGS. 1 through 3, collection device 1 of the present invention comprises a first layer 10 through which fluid can pass, but which does not allow the passage of tissue and blood cells therethrough. First layer 10 thus traps most blood clots, endometrial sloughed tissue and other shed cells but allows fluid to flow through to a fluid retention layer 20 positioned adjacent first layer 10. Preferably, fluid passing though first layer 10 is substantially trapped within fluid retention layer 20. Tissue, blood, tissue and sloughed cells on first layer 10 can be sent for pathological examination if desired.

First layer 10 is preferably lint free, biocompatible and non-antigenic. Preferably, first layer 10 is fabricated from a non-woven cloth (for example, pressed fiber and/or polymeric fiber non-woven materials) and acts as a one-way filter via, for example, capillarity. The non-woven cloth of first layer 10 can be coated with a porous polytetrafluoroethylene (PTFE) coating. A PTFE coating reduces or eliminates the risk of first layer 10 sticking to cervical or vaginal tissue. First layer 10 can also be fabricated from a porous polymeric film that has been pore controlled or micro perforated (for example, perforated by laser perforation to a known pore size) such that blood clots and endometrial sloughed tissue cannot pass therethrough but fluid can flow therethrough to fluid retention layer 20. For example, a pore size of approximately 5 µm is suitable.

Device 1 also comprises a second, outer layer 40 that is preferably fabricated from an impervious, biocompatible latex. A number of such materials have already received governmental approval for intravaginal use by the FDA. Fluid retention layer 20 is preferably completely encompassed by first layer 10, adapter ring 60 and outer second layer 40.

Preferably, the perimeter of first layer 10 and layer 40 is defined by and attached to a resilient rim or adapter ring 60. Adapter ring 60 is compressed by the user as known with other intravaginal collection devices such as diaphragms (see, for example, U.S. Pat. No. 5,295,984) when inserted into the vagina. Upon insertion, device 1 is held into place in a cup-like form (see FIG. 3) by compression of the vaginal wall on adapter ring 60. When device 1 is inserted, first layer 10 faces the cervix, while second layer 40 projects into the vaginal vault.

Adapter ring 60 may, for example, comprise a metallic hoop spring covered by an impermeable, biocompatible material, preferably a biocompatible elastomeric material. In a preferred embodiment, an inner core 80 of adapter ring 60 comprises a resilient foamed polymeric material covered by a biocompatible elastomeric material layer 70 (see FIG. 1). Such a resilient foamed polymeric material is generally more compliant than a hoop spring and can more easily conform to the vaginal wall to reduce the chance of leakage.

Preferably, device 1 is provided in several sizes (diameters) as is the case for contraceptive diaphragms. For example, device 1 may be available in 65, 70, 75, 80 and 85 mm sizes. An initial fitting for device 1 can be performed by a physician. The physician may also discuss with the user a schedule of when the user may periodically bring in specimens collected by device 1 for pathological study. When device 1 is in place, device 1 may or may not be in contact with the cervix depending upon the anatomy of the individual, the size of the cervix and the position in the vaginal cul de sac.

After use, device 1 is preferably removed as with a diaphragm and deposited in a leak-proof and water-proof container for disposal or transportation (for example, to a physician) such as disclosed in U.S. Pat No. 5,287,960. In that regard, a number of diseases, including hepatitis and AIDS, are possibly transmitted via vaginally discharged tissue and blood.

As discussed above, adjacent first layer 10 is fluid retention layer 20. Preferably, the material of fluid retention layer 20 is sufficiently absorbent to be compactly (that is, thinly) constructed. Fluid retention layer 20 also preferably closely approximates the shape of first layer 10 and is very flexible, both when dehydrated and when hydrated. Fluid retention layer 20 is preferably fabricated from an absorbent material such as a flexible, non-woven cloth and/or filter paper. Absorbent fluid retention layer 20 may also, for example, comprise a combination of cellulose and rayon or a sponge-like material.

Several devices 1 are preferably used during the course of the menstrual period (typically, a five-day period). For the convenience of the user, preferably no more than approximately ten devices 1 are necessary for use during one menstrual period. More preferably, approximately five devices 1 are required. To illustrate, the average expected volume of discharged fluid during an entire menstrual period is approximately 55 cc. Fluid retention layer 20 is preferably suitable to retain at least approximately three times the amount of fluid expected during use thereof. For example, if five devices 1 are expected to be used during an entire menstrual period, one would expect on average that approximately 11 cc of fluid will be retained by fluid retention layer 20 of each device 1. Fluid retention layer 20 is, therefore, preferably designed to retain at least 33 cc of fluid. More preferably, fluid retention layer 20 is suitable to retain approximately 35 to 45 cc of fluid or approximately 1 to 1.5 fluid ounces. Retention of such an amount or fluid allows use of device 1 for at least approximately 12 hours even during periods of "heavy flow."

First layer 10 and/or fluid retention layer 20 are preferably treated and/or contain an antibacterial agent such as halogen ions (that is, F, Cl, Br and/or I). These ions, when present in small concentration (for example, as a salt), act to kill the organisms that cause toxic shock. Iodine, as one of its nonstaining salts, has been used in douches and washes for the vaginal area for decades and tends to be non irritating. Cervical and/or vaginal tissues have very little chance to have contact with these salts as the salts are preferably physically or chemically retained (via, for example, adsorption and absorption) by the material of fluid retention layer 20.

The device of the present invention generally provides greater capacity and safety that prior vaginal discharge collection devices. Moreover it is simpler and less messy to insert, use and remove.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A device for the collection of vaginal discharge, the device comprising:
    a. a first layer, the first layer adapted to allow passage of fluid therethrough while substantially preventing the passage of tissue and blood cells therethrough,
    b. a rim attached to the perimeter of the first layer, the rim being sufficiently resilient to provide an outward resilient force suitable to maintain the device in position within a user's vaginal canal during use,
    c. a second layer attached at the perimeter of the second layer to the rim, the second layer adapted to substantially prevent the passage of fluid therethrough, and
    d. a fluid retention layer positioned between the first layer and the second layer, the fluid retention layer being suitable for retaining fluid passed through the first layer.

2. The device of claim 1 wherein the first layer comprises a non-woven material.

3. The device of claim 2 wherein the non-woven material is coated with polytetrafluoroethylene.

4. The device of claim 1 wherein the first layer comprises a porous polymeric material having pores sized to allow passage of fluid therethrough while substantially preventing the passage of tissue and blood cells therethrough.

5. The device of claim 1 wherein the first layer comprises an antibacterial agent.

6. The device of claim 1 wherein the fluid retention layer comprises an antibacterial agent.

7. The device of claim 1 wherein the rim comprises an inner core comprising a resilient foamed material and an outer layer comprising an elastomeric material.

8. The device of claim 1 wherein the fluid retention layer comprises an absorbent material adapted to retain approximately 35 to 45 cc of fluid.

* * * * *